(12) United States Patent
Harmalker et al.

(10) Patent No.: US 7,012,050 B2
(45) Date of Patent: Mar. 14, 2006

(54) SKIN CLEANSING COMPOSITION COMPRISING A QUATERNIZED LANOLIN

(75) Inventors: Subhash Harmalker, Somerset, NJ (US); Tracey Aldrich, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/313,734

(22) Filed: Dec. 6, 2002

(65) Prior Publication Data

US 2004/0110651 A1 Jun. 10, 2004

(51) Int. Cl.
*C11D 1/645* (2006.01)

(52) U.S. Cl. .............. 510/151; 510/119; 510/121; 510/130; 510/133; 510/137; 510/504

(58) Field of Classification Search .......... 510/119, 510/121, 130, 133, 137, 151, 504
See application file for complete search history.

(56) References Cited

U.S. PATENT DOCUMENTS 4,490,355 A * 12/1984 Desai ................ 424/70.19
4,636,571 A * 1/1987 Harris et al. ............ 549/484
4,880,618 A * 11/1989 Grollier et al. ............ 424/43
5,141,803 A * 8/1992 Pregozen ................ 442/123
5,558,873 A * 9/1996 Funk et al. .............. 424/401
5,900,229 A * 5/1999 Dupuis ................... 424/47
6,090,773 A   7/2000 Lukenbach et al.
6,489,286 B1  12/2002 Lukenbach et al.

FOREIGN PATENT DOCUMENTS

| EP | 0 127580 | 12/1984 |
| EP | A 0 463 780 | 1/1992 |
| GB | 1590012 | 5/1981 |
| JP | 4066522 | 2/1992 |
| JP | HEI 6-312915 | 11/1994 |
| WO | WO 00/45787 | 10/2000 |
| WO | WO 03/72692 | 4/2003 |

* cited by examiner

*Primary Examiner*—Charles Boyer
(74) *Attorney, Agent, or Firm*—Kristyne A. Bullock

(57) ABSTRACT

A cleansing composition comprising
(a) a cleansing amount of a surfactant or mixture of surfactants,
(b) a skin slip inducing amount of a quaternized lanolin or mixture of quaternized lanolins, and
(c) a skin slip enhancing inducing amount of a further cationic material or a mixture of cationic materials.

7 Claims, No Drawings

SKIN CLEANSING COMPOSITION COMPRISING A QUATERNIZED LANOLIN

BACKGROUND OF THE INVENTION

Cleansing compositions have been beneficial to mankind for centuries. Basic cleansing has, therefore, been accomplished. Presently, people are desiring an effect beyond that of simple cleansing.

It has now been found that the incorporation of a quaternized lanolin, specifically Quaternium 33 i.e., lanolin amidopropyl dimethyl ether ammonium ethosulfate, preferably with a further quaternary material into a water rinse-off skin cleansing composition brings about an effect easily detectable by people and also enjoyable. This effect, a sensorial skin feel signal (skin slip) observed during and after use of a water rinse-off composition such as in a shower, leaves the skin feeling soft and smooth. The Quaternium 33 is not a classical emollient which are water insoluble but is rather water soluble and its effect is substantially amplified by the addition of other water soluble cationic materials, for example Polyquaternium-7 and a quaternized guar such as guar gum (2-hydroxypropyl-2-hydroxy-3-(trimethylammonium) propyl ether. Softness and smoothness is associated with a moisturizing benefit. Deposition of the material on skin can be detectedby a particular test system. In addition, the combination of cationic materials provides the desired aesthetics of a single phase as well as "stand up" properties of a liquid or gel formulation. The combination can be readily added to the liquid or gel composition in a fragrance without the assistance of further emulsifying agents and at room temperature. Fragrance substantivity on the skin can be enhanced by using the combination of cationic materials.

SUMMARY OF THE INVENTION

In accordance with the invention, there is a cleansing composition comprising, (a) a cleansing amount of a cleansing surfactant or mixture of surfactants, (b) a skin slip inducing amount of a quaternized lanolin or mixture of quaternized lanolins, and (c) a skin slip enhancing inducing amount of at least one further cationic material or a mixture of cationic materials.

DETAILED DESCRIPTION OF THE INVENTION

The cleansing composition can come in any convenient form such as a solid, liquid, gel, spray, aerosol, foam and the like. A cleansing surfactant or mixture of surfactants are employed in the composition to bring about a cleansing effect when applied to the skin and preferably rinsed off with water. These "rinse off" compositions can be rinsed off the skin in less than about one minute, preferably less than about 45, 30 or 15 seconds after application.

Examples of cleansing surfactants which can be employed in the composition include anionic, nonionic, amphoteric and cationic and any mixture thereof.

Any anionic surfactant can be employed. Examples of such anionic surfactants include soap, a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art for example taurates, phosphate, and those listed in the *Mr. Cutcheon's Encyclopedia of Surfactants*.

Other surfactants may be present in the composition. Examples of these surfactants include zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

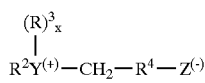

wherein $R^2$ contains an alkyl, alkenyl, or hydroxy alkyl radical of from about 8 to about 18 carbon atoms, from 0 to about 10 ethylene oxide moieties and from 0 to 10 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3 hydroxypentane-1-sulfate
3-[P,P,P-diethyl-P 3,6,9 trioxatetradecyl-phosphonio]-2-hydroxypropane-1-phosphate
3-[N,N-dipropyl-N-3 dodecoxy-2-hydroxy-propylammonio]-propane-I-phosphonate 3-(N,N-di-methyl-N-hexadecyl-ammonio)propane-1-sulfonate; 3-(N,N-dimethyl-N-hexadecylammonio)-2-hydroxypropane-1-sulfonate 4-(N,N-di(2-hydroxyethyl)-N-(2 hydroxydodecyl)ammonio]-butane-1-carboxylate 3-[S-ethyl-S-(3-dodecoxy-2-hydroxy-propyl)sulfonio]-propane-1-phosphate 3-(P,P-dimethyl-P-dodecylphosphonio)-propane-1-phosphonate; and 5-[N,N-di(3-hydroxypropyl)-N-hexadecyl-ammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:
   stearyldimethylbenzyl ammonium chloride;
   dodecyltrimethylammonium chloride;
   nonylbenzylethyldimethyl ammonium nitrate;
   tetradecylpyridinium bromide;
   laurylpyridinium chloride;
   cetylpyridinium chloride
   laurylpyridinium chloride;
   laurylisoquinolium bromide;
   ditallow(hydrogenated)dimethyl ammonium chloride;
   dilauryldimethyl ammonium chloride; and
   stearalkonium chloride.

Additional cationic surfactants are disclosed in U.S. Pat. No. 4,303,543. See column 4, lines 58 and column 5, lines 1–42, incorporated herein by references. Also see *CTFA Cosmetic Ingredient Dictionary*, 6th Edition 1995, pages 795–799 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl)amine oxide, dimethyloctylamine oxide, dimethyidecylamine oxide, dimethyltetradecylamine oxide, 3,6,9 trioxaheptadecyldiethylamine oxide, di(2-hydroxyethyl)-tetradecylamine oxide, 2-dodecoxyethyl-dimethylamine oxide, 3-dodecoxy-2-hydroxypropyldi(3-hydroxy-propyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond.

Examples of suitable phosphine oxides are:
dodecyldimethylphosphine oxide, tetradecylmethylethylphosphine oxide,
3,6,9-trioxaoctadecyldimethyl-phosphine oxide, cetyldimethylphosphine oxide, 3-dodecoxy-2-hydroxypropyldi(2-hydroxyethyl)phosphine oxide stearyldimethyl-phosphine oxide,
cetylethyl propylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxy-ethyl)phosphine oxide,
tetradecyl-methyl-2-droxypropylphosphine oxide,
oleyldimethylphosphine oxide, and
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides include wherein the alkyl group is from about 8 to 20 carbon atoms, preferably about 10 to about 18 carbon atoms and the degree of polymerization of the glycoside is from about 1 to about 3, preferably about 1.3 to about 2.0.

A quaternized lanolin provides the skin sensorial feel that is unique to the composition. Examples are the previously mentioned Quaternium 33, quaternized lanolins with various counterions such as chloro, bromo, nitrate, methosulfate, acetate, lactate, and the like, quaternized lanolins wherein an amidoethyl or amido butyl grouping is used rather than an amido propyl as in Quaternium 33 and diethyl or dipropyl ether ammonium grouping is employed rather than the dimethylether ammonium group of the Quaternium 33.

It is preferable to employ at least one further quaternized material in the composition. This brings about accentuation of the skin slip sensorial feel present with the quaternized lanolin or can lower the minimum amount of quaternized lanolin associated with the skin slip. These further quaternized materials can be cationic materials which include the various polyquats known to the art which include but are not limited to Polyquaternium 2 (a polyelectrolyte formed from quaternized ioenes), Polyquaternium 4 (hydroxycellulose diallyldimethyl ammonium chloride), Polyquaternium 5 (acrylamide/β-methacryloxyethyltrimethyl ammonium methosulfate), Polyquaternium 6 and 7 (homopolymer of dimethyl diallyl ammonium chloride and the copolymer of dimethyl diallyl ammonium chloride with acrylamide), Polyquaternium 8 (methyl and stearyl dimethylaminoethyl methacrylate quaternized with dimethylsulfate), Polyquaternium 10 (1-hydroxypropyl trimethyl ammonium chloride ethers of hydroxyethyl cellulose), Polyquaternium 11 (quaternized PVP and dimethylaminoethyl methacrylate), Polyquaternium 16 (copolymer of PVP/methyl vinylimidazoline), Polyquaternium 17 and 18 (polyelectrolyte formed from quaternized ioenes), Polyquaternium 19 (a vinyl alcohol hydroxypropyl amine salt), Polyquaternium 24 (polymeric quaternized ammonium salt of hydroxymethylcellulose and lauryl dimethyl ammonium substituted epoxide), Polyquaternium 27 (polyelectrolyte formed from quaternized ioenes). Other cationic materials include Polycare 133 (a polymethyacrylamideopropyl trimonium chloride from Rhone-Poulenc). and quaternized guar. Preferably a quaternized guar for example quaternized quar per se, hydroxyethyl quaternized guar and more preferably guar gum (2-hydroxypropyl-2-hydroxy-3-(trimethylammonium)propyl ether is employed.

A cleansing effective amount of a cleansing surfactant should be employed in the composition. Generally, for liquid or gels, at least about 1 wt. % of the composition should be a surfactant or a mixture of surfactants. Desirably, at least about 2, 3, 4, or 5 wt. % should be employed. For liquids or gels, the quantity of surfactants generally is no more than about 30 wt. % of the composition, preferably no more than about 25, 20, 15 or 12 wt. % of the composition. For solids, an even higher minimum can be used as well, for example, preferably about 10, 20, 30, 40 or 50 wt. % of the composition can be surfactant(s). When a solid composition such as a bar is employed, the maximum amount of surfactant(s) is generally no more than about 90 wt. % of the composition, preferably no more than about 85, 80 or 75 wt. % of the composition. With respect to other forms, such as sprays, aerosols, and the like the quantity of surfactant(s) is similar to that of the liquids or gels with respect to the actual cleansing composition, excluding whatever propellant might be present. With respect to water content, for solids at least about 5 wt. % water is present with generally no more than about 30, 25, 20 or about 15 wt. % water. For liquids and gels, at least about 60 wt. % water is present, preferably about 70 or 80 wt. %.

With respect to the quaternized lanolin, particularly Quaternium 33, any quantity which brings about detectable "skin slip" can be used. With respect to solids, this can be a wt. % minimum of the composition of about 0.1, preferably 0.2, 0.4 and 0.6. Generally, a maximum of about 3 wt. % of the composition, preferably no more than about 2, 1.5 or 1.0 wt. % of the composition is employed. A minimum amount of the quaternized lanolin in liquid or gels is generally about 0.1, preferably 0.25 or 0.5 wt. % of the composition. Maximum quantities of the quaternized lanolin is generally no more than 2.5 wt. %, preferably no more than about 1.0 or 0.5 wt. %.

The additional cationic materials present in the composition in quantities which reduce the amount of quaternized lanolin necessary to bring about skin slip or enhance the quantity of skin slip brought about by the quaternized lanolin. With respect to solids, this can be a wt. % minimum of the composition of about 0.1, preferably 0.2 and 0.4. Generally, a maximum of about 2 wt. % of the composition, preferably no more than about 1.5 or 1 wt. % of the composition is employed. A minimum amount in liquids or gels is generally about 0.1, preferably 0.2 or 0.4 wt. % of the composition. Maximum quantities of the material are generally no more than about 2 or 1 wt. % of the composition.

As with the surfactants, the quantities of the quaternized lanolin and additional quaternized material will vary in the same manner with respect to the other form such as sprays and aerosols. It should be noted that in referring to liquids and gels, these are the delivered compositions which are delivered by the spray or aerosol to the skin. Therefore, for these delivery systems, the quantity is calculated on the composition apart from the materials that make up the spray or the aerosol components.

Additional materials can be present in the composition including but not limited to fragrances, colorants, preservatives, thickeners, antibacterial compounds and the like.

Approximately 0.5 wt. % each of potential skin conditioning agents were tested in an aqueous cleansing composition as shown below.

Below are examples and various comparative examples of the invention.

EXAMPLE 1

| Component | Wt. % |
|---|---|
| Sodium laureth 2-sulfate | 8.2 |
| Cocoamido propyl betaine | 3.0 |
| Decylpolyglucoside | 1.1 |
| Sodium chloride | 1.0 |
| Ethylene Glycol Distearate | 0.875 |
| Potential Skin Conditioning Agent | 0.5 |
| PolyQuaternium-7 | 0.2 |
| Preservative, colorant, chelant, fragrance | 1.2 |
| Water | q.s. |

These agents were the following:
Lanolin
Laneth-5
Laneth-15
PPG-12-EG-50 Lanolin
Di-ppg-3-myristyl ether adipate
Soydimonium hydroxypropyl hydrolysed wheat protein
Hydroxypropyl trimonium honey
Hydrolyzed whole oats
Hydroxypropyltrimonium hydrolyzed wheat protein
Hydroxypropyltrimonium hydrolyzed wheat starch
Sodium isostearyl lactate
Quaternium 33

The following protocol was used for testing the skin conditioning properties.
1. Rinse arm under tap water at 75–80° F.
2. Apply 1 ml product via syringe (topically).
3. Spread product on arm by gently rubbing it with fingers for 30 seconds.
4. Record skin feel (slippery smooth) as none, slight, somewhat, significant during rubbing.
5. Rinse-off product from arm.
6. Air dry and record skin feel after about one hour after several finger rubs.

The results demonstrated that Quaternium 33 was clearly superior to any of the other tested agents for providing a skin feel, in this case skin slip, after the washing and for a period of time after the rinse-off (for approximately at least one hour).

EXAMPLE 2

A comparison was made to establish the significance of the second cationic material. A water rinse off composition, the same as used in Example 1 without any cationic material as used as the base composition. To this base was added various cationic materials as shown below together with the test results.

Results

| Composition | Skin Feel* (Slippery Smooth) |
|---|---|
| 1. Q33 | Somewhat |
| 2. Polyquat-7 | Slight |
| 3. Guar quat | Slight |
| 4. Guar quat + Q33 | Somewhat |
| 5. Q33 + PQ-7 + Guar Quat. | Significant |

Rating Scale: None < Slight < Somewhat < Significant

Protocol

The same protocol is used for testing the skin conditioning properties in Example 1 was used in this example.

The invention claimed is:

1. A rinse off skin cleansing composition comprising:
   (a) a cleansing amount of a cleansing surfactant or mixture of surfactants,
   (b) a skin slip inducing amount of a quaternized lanolin or mixture of quaternized lanolins, and
   (c) a skin slip enhancing inducing amount of a further cationic material or a mixture of cationic materials selected from the group consisting of Polyquaternium 2 (a polyelectrolyte formed from quaternized ioenes), Polyquaternium 4 (hydroxycellulose diallyldimethyl ammonium chloride), Polyquaternium 5 (acrylamide/ β-methacryloxyethyltrimethyl ammonium methosulfate), Polyquaternium 6 and 7 (homopolymer of dimethyl diallyl ammonium chloride and the copolymer of dimethyl diallyl ammonium chloride with acrylamide), Polyquaternium 8 (methyl and stearyl dimethylaminoethyl methacrylate quaternized with dimethylsulfate), Polyquaternium 10 (1-hydroxypropyl trimethyl ammonium chloride ethers of hydroxyethyl cellulose), Polyquaternium 11 (quaternized PVP and dimethylaminoethyl methacrylate), Polyquaternium 16 (copolymer of PVP/methyl vinylimidazoline), Polyquaternium 17 and 18 (polyelectrolyte formed from quaternized ioenes), Polyquaternium 19 (a vinyl alcohol hydroxypropyl amine salt), Polyquaternium 24 (polymeric quaternized ammonium salt of hydroxymethylcellulose and lauryl dimethyl ammonium substituted epoxide), Polyquaternium 27 (polyelectrolyte formed from quaternized ioenes), Polycare 133 (a polymethyacrylamidopropyltrimonium chloride), and guar gum (2-hydroxypropyl-2-hydroxy-3-(trimethylammonium) propyl ether.

2. The composition in accordance with claim 1 wherein the composition is a solid, liquid or gel.

3. The composition in accordance with claim 2 wherein the quaternized lanolin is Quaternium 33.

4. The composition in accordance with claim 2 wherein the cationic material is a quaternized guar.

5. The composition in accordance with claim 4 wherein the quaternized guar is guar gum (2-hydroxypropyl-2-hydroxy-3-(trimethylammonium)propyl ether.

6. The composition in accordance with claim 2 wherein when the composition is a bar at least about 5 wt. % of surfactant is present and when the composition is a liquid or a gel at least about 1 wt. % of surfactant is present in the composition.

7. A method for cleansing skin which comprises
   (a) applying the composition of claim 1 to the skin in the contact presence of water, and
   (b) rinsing the composition from the skin with water.

* * * * *